(12) United States Patent
Rantala (10) Patent No.: US 7,881,778 B2
(45) Date of Patent: Feb. 1, 2011

(54) FLOATING PHYSIOLOGICAL DATA ACQUISITION SYSTEM WITH EXPANDABLE ECG AND EEG

(75) Inventor: Börje Rantala, Helsinki (FI)

(73) Assignee: The General Electric Company, Schenectady, NY (US)

(*) Notice: Subject to any disclaimer, the term of this patent is extended or adjusted under 35 U.S.C. 154(b) by 301 days.

(21) Appl. No.: 11/528,919

(22) Filed: Sep. 28, 2006

(65) Prior Publication Data

US 2008/0081960 A1    Apr. 3, 2008

(51) Int. Cl.
*A61B 5/04* (2006.01)
(52) U.S. Cl. .................................... 600/509
(58) Field of Classification Search ............... 600/301, 600/483, 508, 509
See application file for complete search history.

(56) References Cited

U.S. PATENT DOCUMENTS

| | | | | |
|---|---|---|---|---|
| 4,974,162 A * | 11/1990 | Siegel et al. | ............... | 600/509 |
| 5,231,990 A | 8/1993 | Gauglitz | | |
| 5,307,817 A | 5/1994 | Guggenbuhl et al. | | |
| 5,704,351 A * | 1/1998 | Mortara et al. | ............... | 600/382 |
| 6,083,156 A * | 7/2000 | Lisiecki | ................ | 600/301 |
| 7,146,205 B2 | 12/2006 | Holman | | |
| 2002/0183634 A1 * | 12/2002 | Rantala et al. | .............. | 600/509 |

FOREIGN PATENT DOCUMENTS

| | | |
|---|---|---|
| EP | 1 221 299 | 7/2002 |
| GB | 2272770 A | 5/1994 |
| WO | 89/02247 A1 | 3/1989 |
| WO | WO 01/06923 | 2/2001 |

OTHER PUBLICATIONS

U.K. Search Report for corresponding Great Britain Patent Application No. GB0718719.8 dated Jan. 23, 2008.

* cited by examiner

*Primary Examiner*—George R Evanisko
*Assistant Examiner*—Michael D'Abreu
(74) *Attorney, Agent, or Firm*—Andrus, Sceales, Starke & Sawall, LLP

(57) ABSTRACT

A floating physiological data acquisition system with expandable ECG and EEG. The data acquisition system for obtaining electrophysiological signals from a patient comprises a patient monitor and separate patient side acquisition units connectable to the patient monitor. Each of the patient side acquisition units comprises an analog-to-digital converter, a serial interface communicative towards a serial bus connecting the patient side data acquisition unit with the patient monitor, and a serial interface controller processor. Each of the patient side acquisition units further forms a part of a floating patient applied part of the data acquisition system.

12 Claims, 5 Drawing Sheets

PRIOR ART

FLOATING PHYSIOLOGICAL DATA ACQUISITION SYSTEM WITH EXPANDABLE ECG AND EEG

FIELD OF THE INVENTION

The invention relates to a modular data acquisition system for obtaining physiological signals from a patient. The modular data acquisition units can be added to the system by a serial interface that communicates towards a serial bus thus forming a part of a floating patient applied part of the data acquisition system.

BACKGROUND OF THE INVENTION

Electrocardiography (ECG) measures the electrical activity of the heart. It depicts the rate and the regularity of heartbeat as well as the presence of cardiac diseases or damage, arrhythmias etc. The ECG is one of the most important non-invasive diagnostic tools available to the cardiologists. It is measured by placing electrodes on the chest of the patient and measuring the bioelectrical potentials produced by the heart. Electrodes attached to the patient are connected by leads to an ECG monitor for further signal processing.

Figure 1:
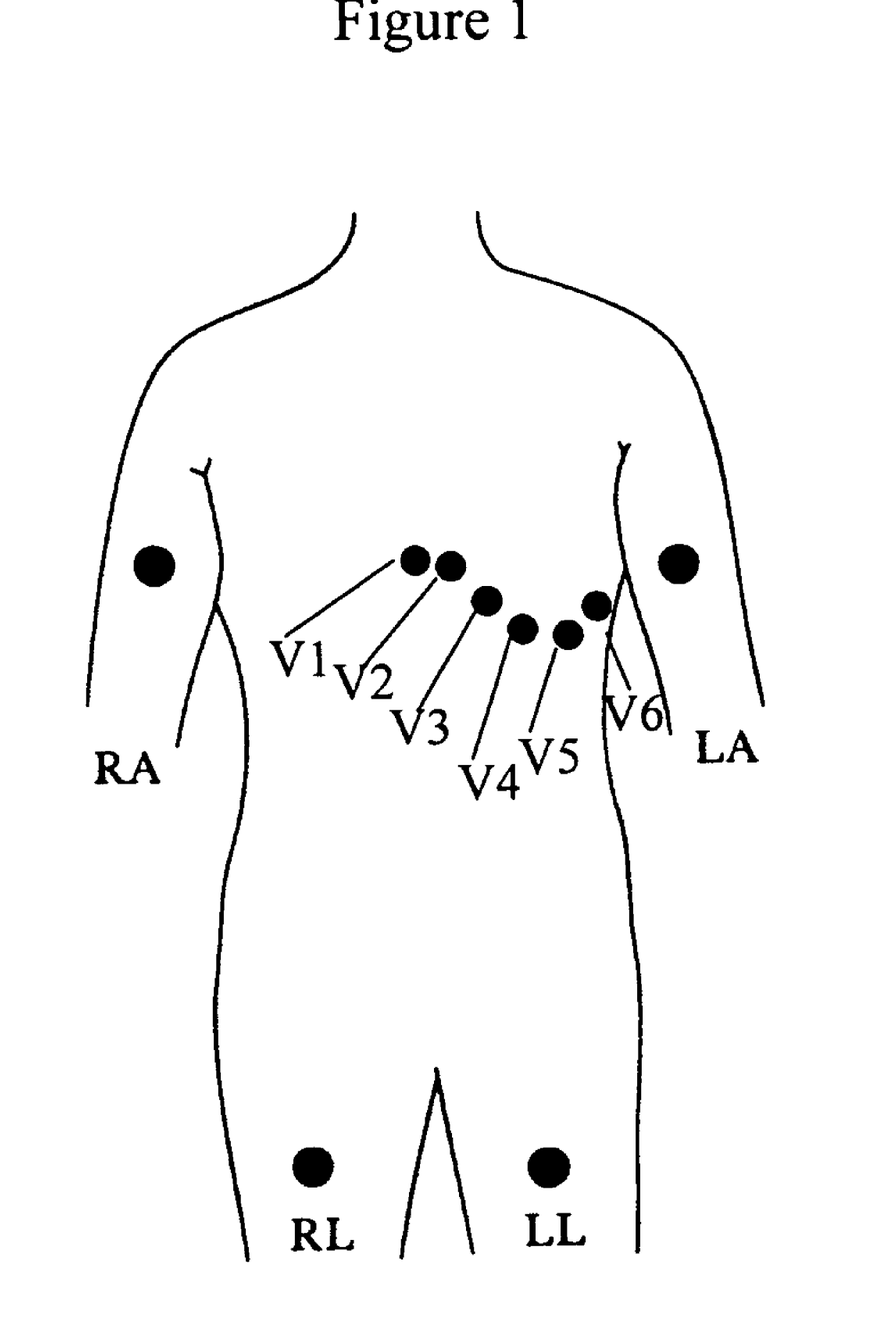
FIG. 1 depicts the standard electrode placement of a 12 lead ECG measurement.

Standard methods for obtaining an ECG from a subject are 3 lead, 5 lead, 12 lead or a 15 lead ECG. 3 lead and 5 lead ECG are commonly used for routine ECG monitoring at hospitals. The 12 lead ECG recording provides much more information e.g. about possible cardiac ischemia than is obtainable from the 3 or 5 lead ECG. Therefore, the 12 lead ECG is the most common of these methods and thus often referred to as the "standard 12 lead ECG". The 5 lead measurement provides seven signals: the limb leads I, II, III, aVR, aVL, aVF and one precordial lead e.g. V5. This measurement can be done by placing one electrode to each of the patient's four limbs at the wrists and ankles and one precordial electrode to the patient's chest. The limb electrodes are referred to as left arm (LA), right arm (RA), left leg (LL), and right leg (RL). For a standard 12 lead ECG, ten electrodes are attached to a patient's body in a manner described in FIG. 1. As shown in FIG. 1, six electrodes are attached in standard positions on the chest around the heart. The standard 12 lead ECG thus provides information from the frontal plane from limb leads I, II, III, aVR, aVL and aVF and from the horizontal plane from precordial leads V1, V2, V3, V4, V5 and V6. As is commonly known in the art, the ten electrodes are connected via lead wires and resistor networks to amplifiers to record twelve separate ECG channels or leads.

The frontal leads are obtained with various permutations of the LA, RA, and LL electrodes, with the RL electrode serving as an electrical ground. The frontal leads are comprised of the potential between two of the limb electrodes: lead I corresponds to the potential between LA and RA, lead II corresponds to the potential between LL and RA, and lead III corresponds to the potential between LL and LA. Leads aVR, aVL, and aVF, referred to as the augmented leads, are comprised of the potential between one electrode and a reference input, the reference input being the average of two electrodes. For example, lead aVF is the signal between LL and a reference input, where the reference input is the average of the potentials at electrodes RA and LA.

Figure 2:
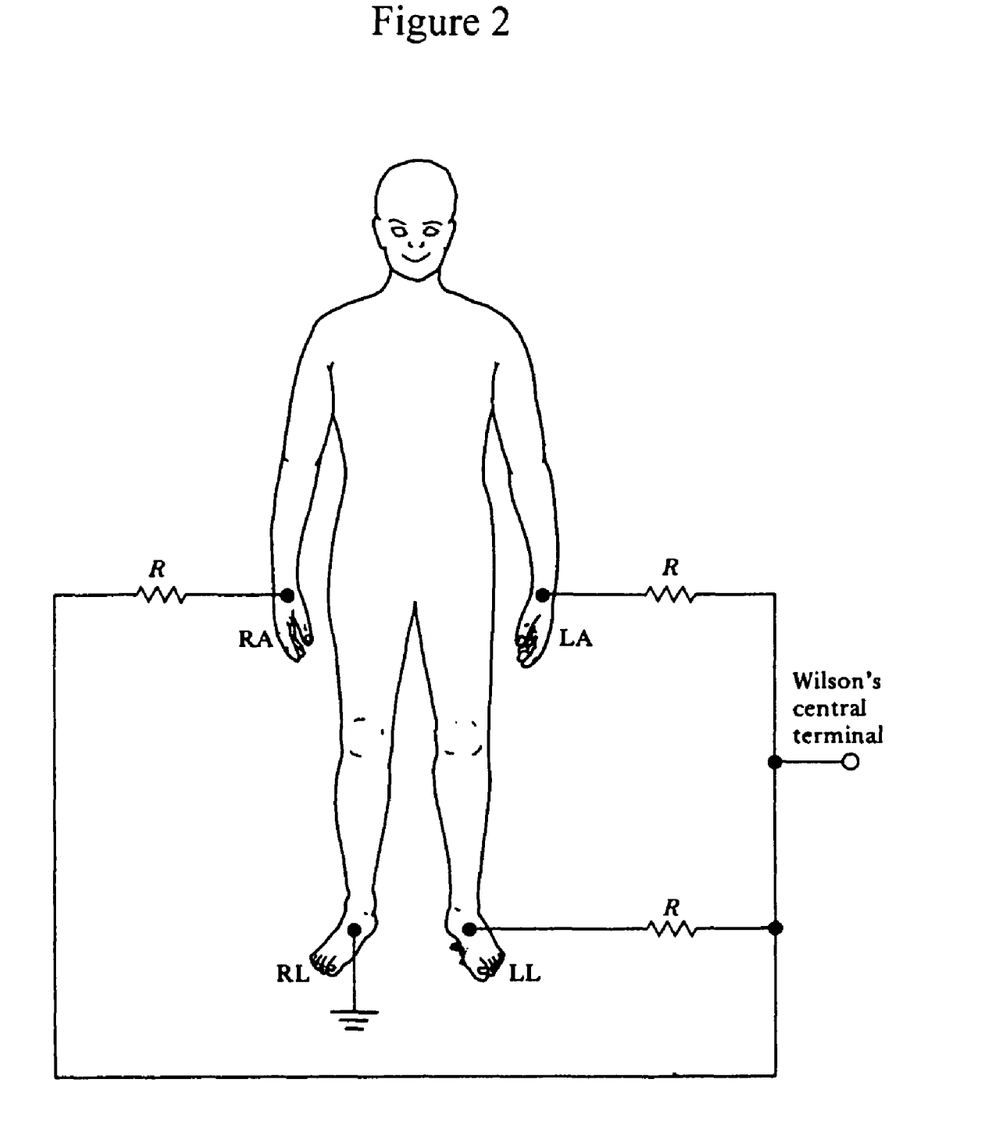
FIG. 2 depicts simplified the connection of electrodes to the body to obtain Wilson's central terminal.

The horizontal leads V1-V6 are obtained with various permutations of the six electrodes attached to the patient's chest, in addition to three of the four limb electrodes. Each of the six horizontal leads is comprised of the signal between the potential at the particular electrode placed on the patient's chest and the potential at Wilson's central terminal. Wilson's central terminal refers to the average potential between the RA, LA, and LL electrodes shown simplified in FIG. 2. The three limb electrodes are connected through equal valued resistors to a common node and the voltage at this node, the Wilson central terminal, is the average of the voltages at each electrode. Each of the leads V1-V6 is compared to Wilson terminal, for example, lead V1 is the signal between electrode V1 and Wilson's central terminal.

It is not always clear when beginning the treatment how close monitoring will be needed in the future. The patient may go under a preliminary examination and a 3 or 5 lead ECG may be applied. Sometimes further examinations are needed e.g. for eliminating certain illnesses that can be detected by recording 12 lead ECG. Changing from 5 lead ECG to 12 lead ECG may be time consuming and difficult. Changing the electrode set and detaching and reattaching the electrodes can take considerable time, particularly if carried out by a non-specialist. This problem could be solved by always using the 12 lead or the 15 lead ECG electrode set and cable and only using the electrodes that are needed for that particular measurement. However, the 12 lead and the 15 lead ECG measurement cables are typically thick and long which makes the nursing staff favor the smaller and more convenient 5 lead ECG measurement electrode set. It is not desirable to have heavy wiring and plurality of unnecessary electrodes if the measurement accuracy of a 12 lead ECG is not needed.

In addition, if an EEG signal is to measured during examination, it will be a burden to the nursing staff to bring a separate EEG device for the measurement. The examination room or the operating room will get crowded if too many separate measuring equipment are needed.

In attempt to solve these problems, several solutions have been developed.

WO 01/06923 describes a system for ECG monitoring which enables the change between measuring 5 lead ECG and 12 lead ECG. In the measurement system described in the publication the 5-lead ECG is measured by connecting measuring electrodes by signal leads connected to a first connector element in a collecting connector. A second connector element of the collecting connector acts then as a shielding ground connection for the leads. A 12-lead ECG signal can be acquired by connecting additional measurement electrodes by leads to the second connector element of the collecting connector. The measurement signals are passed from the collecting connector to an amplifier unit and to the ECG apparatus for signal processing. The problem with the method described in the publication is that the lead wires when measuring 12 lead ECG will not be shielded and isolation of the system will be needed to ensure complete patient safety.

Publication EP 1221299 describes a method and an apparatus for generating a 12 lead ECG from fewer than ten electrodes. The method and apparatus of the publication generates a plurality of leads that are the same as the leads that would be generated from the electrical signals of a standard ECG. In the most preferred embodiment of the publication, electrodes V2, V3, V4, and V6 are not attached to the patient. Thus, leads V2, V3, V4, and V6 corresponding to the omitted electrodes must be derived mathematically by using multiple-linear regression. Eight of the leads, namely leads I, II, III, aVR, aVL, aVF, V1, and V5, are generated in the same manner as in a standard ten-electrode, twelve-lead ECG. In general, the four missing leads are calculated by using multiple-linear regression based on the relationship between the available leads and a data set of previously acquired ECGs. Although enabling the change between 5 lead ECG and 12 lead ECG, reducing the number of electrodes and calculating the signal for the missing leads may bring uncertainty in the ECG signal.

As is evident from the above, prior art solutions have several limitations and disadvantages.

PURPOSE OF THE INVENTION

The purpose of the present invention is to provide a simple and reliable system and method for a floating patient data acquisition system with expandable ECG and EEG.

SUMMARY OF THE INVENTION

The invention relates to a floating patient data acquisition system with expandable ECG and EEG. The data acquisition system according to the present invention comprises a patient monitor and at least one separate patient side acquisition unit connectable to the patient monitor. Each of the patient side acquisition units comprises an analog-to-digital converter, a serial interface communicative towards a serial bus connecting the data acquisition unit with the patient monitor, and a serial interface controller processor. Each of the patient side acquisition units further forms a part of a floating patient applied part of the data acquisition system.

The invention also relates to a method for obtaining electrophysiological signals from a patient by using a data acquisition system comprising a patient monitor and at least one separate patient side acquisition unit. The method according to the invention comprises the steps: converting the electrophysiological signal into a digital signal by an analog-to-digital converter in the patient side acquisition unit, connecting the patient side acquisition unit with the patient monitor by a serial interface communicative towards a serial bus, controlling the serial interface by a serial interface controller processor; and forming a part of a floating patient applied part of the data acquisition system with each of the patient side acquisition units. The electrophysiological signal measured by the patient side acquisition unit is referenced to one common point by electrophysiological preamplifiers of said data acquisition units. A common analog Wilson terminal is further arranged to the serial connection from the patient side acquisition units to the patient monitor.

In a preferred embodiment of the invention, the patient side acquisition units form a modular ECG measurement system which comprises a 5 lead ECG measurement unit that is expandable by a 12 lead ECG extension unit. When the signals acquired by the 5 lead ECG measurement unit and the 12 lead ECG extension unit are combined, a full 12 lead ECG signal is formed.

In another embodiment of the invention the serial interface comprises a common analog Wilson terminal for allowing electrophysiological preamplifiers of said data acquisition units to reference measured electrophysiological signal to one common point.

The measurement system may also be expanded by other data acquisition units such as an extension units to measure 15 lead ECG signal or EEG signal.

In another embodiment of the invention the connection from the serial bus to the patient monitor is a wireless connection. If the serial bus has a wired connection, wireless terminal batteries are charged. In addition, patient id is transferred to said patient side acquisition units via a wired connection, thus setting the patient context.

In yet another embodiment of the invention the serial bus is a Universal Serial Bus (USB) which may be augmented by an analog Wilson terminal. The serial bus speed is set to be low enough to allow connection from the data acquisition unit to the patient monitor without a hub electronic connection. When the serial bus speed is low enough, impedance matching is not needed and high frequency reflections can be avoided.

The benefits of the invention are related to the improved reliability and noise reduction of the ECG signal. Having the common Wilson terminal for all data acquisition units and isolating the data acquisition units reduce e.g. diathermy interference and other high frequency noise. A further benefit of the invention is that it allows the medical professionals to start with one measurement and expand the measurement by adding new patient side acquisition units. For example, a 5 lead ECG can be acquired first and in case closer examination is needed, the 5 lead ECG measurement can be expanded merely by applying five additional electrodes provided by the 12 lead ECG extension unit. Since the measurement units use the same common Wilson terminal, the signals may be combined to form a full 12 lead ECG signal. The system provides the possibility to add other data acquisition units depending which signal is needed.

The serial bus connection allows the physiological signals to be transmitted digitally and the Wilson terminal potential will be available to the data acquisition units in analog form. This is important as the preamplifiers of the patient side data acquisition units always need an analog Wilson terminal potential to reference the measured signal with. The serial bus floats in the same potential with the patient and is isolated from the monitor. Isolation is implemented in one place between two serial connections whereas in prior art, isolation is performed in each measurement unit and between analog connection and serial bus connection. In the system according to the present invention, isolation is thus safer and less expensive.

Various other features, objects, and advantages of the invention will further be apparent from the following detailed description and the drawings.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE EMBODIMENTS

Reference will now be made in detail to the embodiments of the present invention, examples of which are illustrated in the accompanying drawings.

Figure 3:
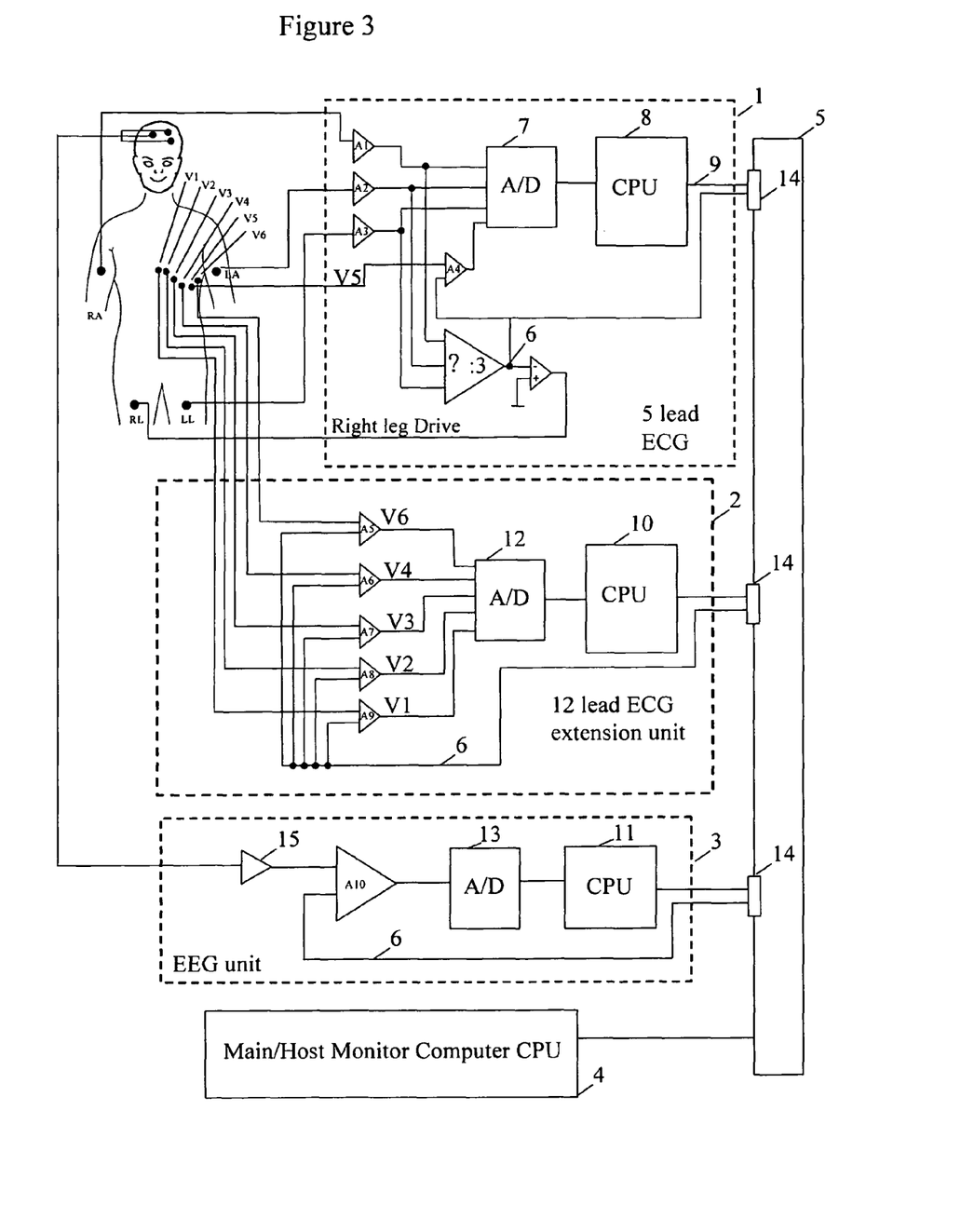
FIG. 3 depicts the data acquisition system according to the present invention that is expandable with separate measurement modules.

The floating ECG measurement system according to the present invention is illustrated in FIG. 3. A 5 lead ECG measurement unit 1 measures the ECG signal from electrodes RA, LA and LL. Augmented leads aVR, aVL and aVF (not shown in FIG. 3) are calculated by comparing the measured voltage from each of the limb electrodes to a reference voltage (the average of the other two electrodes), and the one precordial lead e.g. V5 is comprised by comparing and amplifying the signal measured from that electrode to a common potential i.e. Wilson's terminal in amplifier A4. Wilson's terminal 6 is the calculated average voltage of the three limb leads $V_R$, $V_L$, and $V_F$ (i.e. average potential of RA, LA, and LL) The measured ECG signal is amplified by preamplifiers or the front end amplifiers A1-A4 and it is converted into a digital ECG signal by A/D converter 7. The signal is transmitted to the main monitor computer 4 by serial bus connection 5. The connector element 14 connecting the ECG signal 9 and Wilson's central terminal 6 to the serial bus can be e.g. a mini USB connector. The Wilson's terminal is connected to one of the mini USB pins and further via the serial bus connection 5 to the other modular measurement units (such as the 12 lead ECG extension unit 2 or the EEG measurement unit 3) as well as to the main monitor computer 4. It may also be another type of connector element which is able to carry the ECG signal and the Wilson terminal potential to the serial bus to be transmitted to other data acquisition units.

The measurement system according to the present invention can be expanded to a 12 lead ECG measurement by adding a 12 lead ECG extension unit 2. In the 12 lead ECG measurement, the voltage signal from each electrode V1-V6 is compared to the analog Wilson's terminal potential in the front end amplification A5-A10. As the preamplifiers of ECG measurement units always amplify an analog signal, the Wilson terminal potential must also be in analog form and it can thus not be transmitted as a digitalized signal. To be able to combine the signal from the 12 lead ECG extension unit and the 5 lead ECG measurement unit and form a comprehensive 12 lead ECG, the voltages of each lead V1-V6 is compared to an analog Wilson's terminal potential and the digitalized signal is transmitted by the serial digital communication 5 to main monitor computer 4. The 12 lead ECG extension unit receives the Wilson's terminal potential 6 from the 5 lead ECG unit 1 via the serial bus connection 5. Since all necessary leads of the 12 lead ECG are transmitted via the serial interface 14 and the serial bus connection 5 to the main monitor computer 4, the full 12 lead ECG signal may be reconstructed.

Figure 4A:
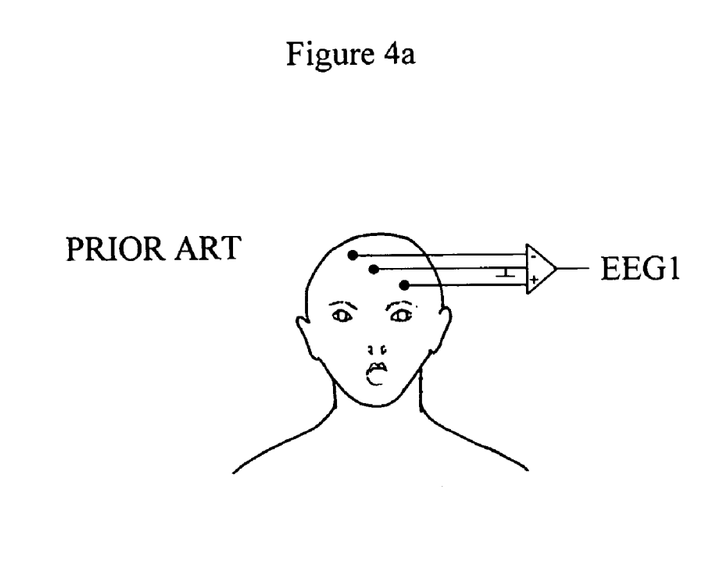
FIG. 4a describes the prior art connection of EEG measurement electrodes.
Figure 4B:
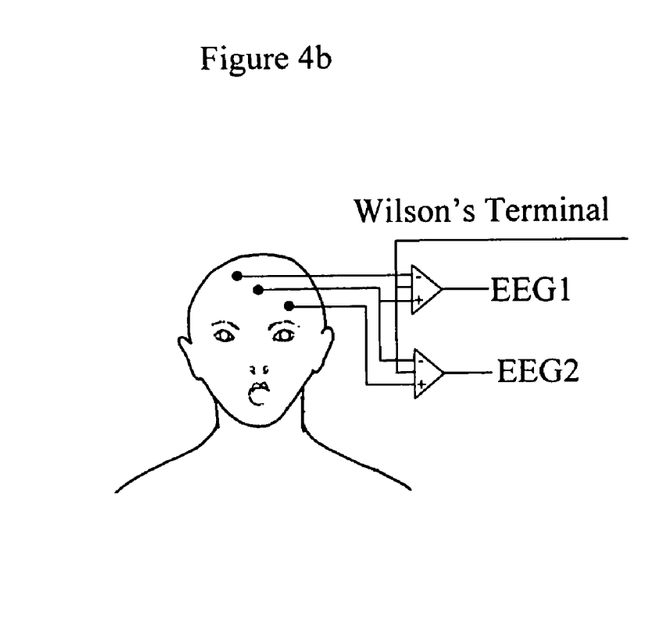
FIG. 4b describes the EEG electrode connection according to the present invention.

The data acquisition system according to the present invention may also be extended by adding a modular EEG measurement unit 3 to the system. The signal acquired from the EEG measurement electrodes use the Wilson's terminal potential 6 as floating ground. This saves one of the measurement electrodes for another EEG channel thus improving the measurement quality. EEG measurement is better described in FIGS. 4a and 4b. FIG. 4a presents prior art EEG measurement in which one of the electrodes must be used as ground for the EEG measurement. The EEG measurement according to the present invention is described in FIG. 4b. Since the measurement can use Wilson's terminal as a floating ground, the invention frees one of the three EEG electrodes and provides an additional channel to the EEG measurement. When adding the EEG measurement unit 3 to the data acquisition system, the EEG signal from the electrodes is amplified by amplifier 15 and then compared (by A10) with the analog Wilson's terminal 6 received from the 5 lead ECG measurement unit 1 via the serial bus connection 5. The EEG signal is converted into a digital signal by A/D converter 13 and transmitted via the serial interface 14 and the serial bus 5 to the main monitor 4.

Figure 5:
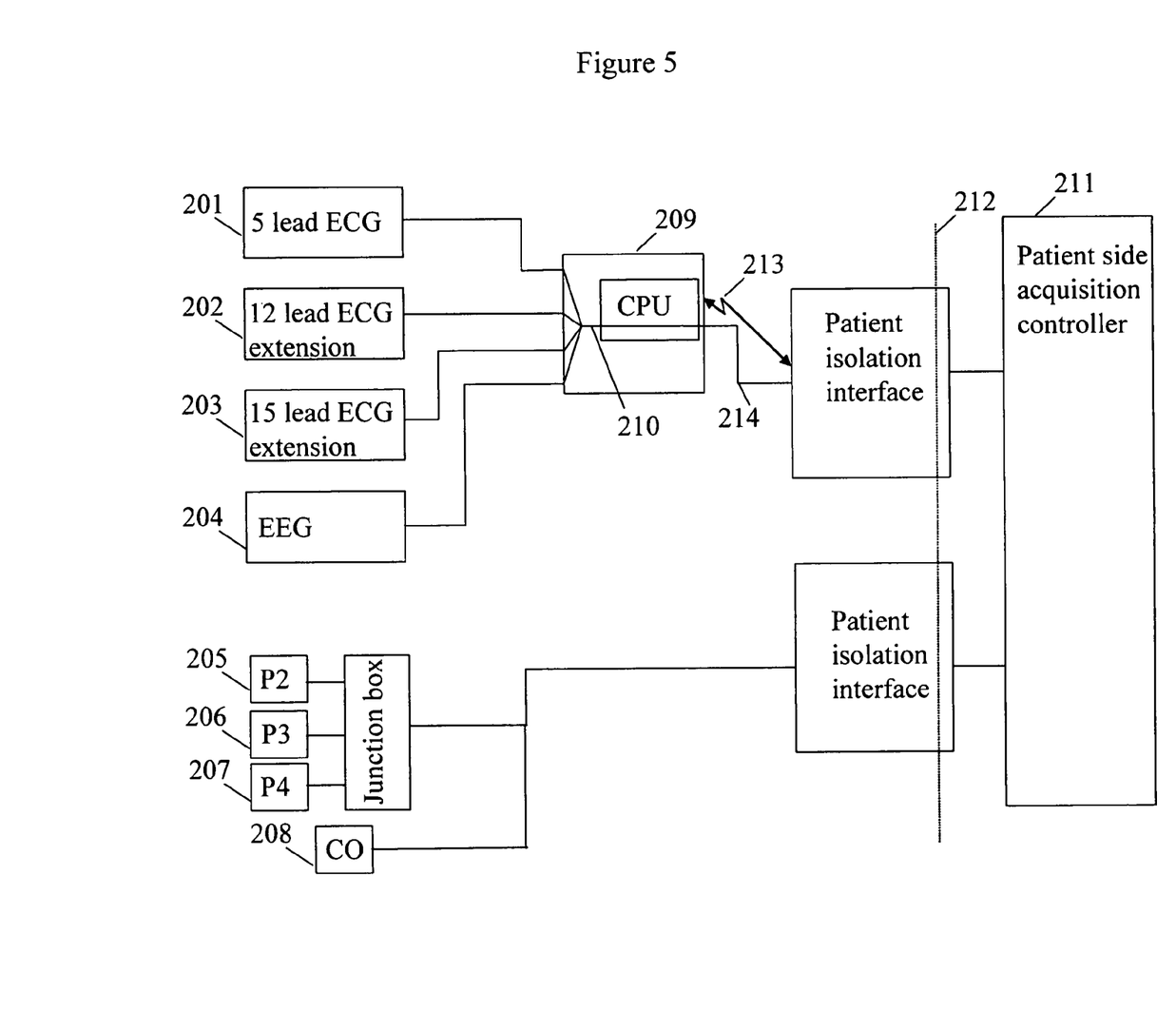
FIG. 5 describes a block diagram of the present modular data acquisition system.

FIG. 5 describes the block diagram of the modular data acquisition system according to the present invention. Measurement units 201-203 are electrically connected and utilize the same Wilson's terminal potential to which they e.g. compare the measured voltages in the front end amplification in order to acquire the horizontal plane ECG signals. The expandable EEG unit 204 may also be electrically connected to the other measurement units 201-203 and use the Wilson terminal potential as a floating ground thus saving one additional electrode to EEG measurement. However, this is not necessary and the EEG measurement unit may revert to using one of the EEG electrodes as a common ground electrode, especially if the ECG monitoring module is removed in the middle of ongoing monitoring, or if the ECG is noisy. The modules 201-204 are all connected via a serial bus connection 210 and the collected signals may further be transmitted either by using smart cables 214 or wireless connection 213. The dotted line 212 depicts the isolation interface to the patient floating side. Isolation provides a barrier for the current from the power line (50-60 Hz) and prevents dangerous currents from flowing from the patient through he amplifier to the ground of the monitor. The isolation is normally implemented by using optoisolators, electrical transformers or other isolation method. Other measurement signals such as the pressure signals 205-207 and cardiac output signal 208 are independent from the Wilson terminal potential and are thus connected via a separate serial connection to the patient side acquisition controller 211. They are also isolated from the monitor to protect the system from high frequency electrical interference. The serial bus connection 210 floats in the same potential with the patient and isolation interface can be arranged in one point between the patient and the main monitor which carries digitalized serial communication.

It must be contemplated that the above embodiments of the invention are presented here as examples and that the basic idea of the invention may vary within the scope of the claims. It will also be evident to a person skilled in the art that with the advancement of technology, the idea of the invention may be implemented in various other ways. The invention and its embodiments are thus not limited to the examples described above; instead they may vary within the scope of the claims.

The invention claimed is:

1. A data acquisition system for obtaining electrophysiological signals from a patient, the system comprising:
   a serial bus;
   a first connector element connected to the serial bus;
   a first signal acquisition unit connected to the first connector element and configured to receive a first analog signal, a second analog signal, a third analog signal, and a fourth analog signal from a first limb electrode, a second limb electrode, a third limb electrode, and a fourth limb electrode, respectively, and a fifth precordial analog signal from a fifth precordial electrode,
   to amplify said first analog signal, said second analog signal and said third analog signal to yield a first amplified analog signal, a second amplified analog signal and a third amplified analog signal, respectively,
   to compute an average voltage of said first amplified analog signal, said second amplified analog signal and said third amplified analog signal,
   to amplify said fifth precordial analog signal to yield a fifth amplified precordial analog signal,
   to obtain a fifth compared amplified precordial analog signal as the potential difference between said fifth amplified precordial analog signal and said average voltage,
   to convert said first amplified analog signal, said second amplified analog signal, said third amplified analog signal, and said fifth compared amplified precordial analog signal to digital form to yield a digital signal, to provide said digital signal via a connector element to said serial bus, and to provide said average voltage via said first connector element to said serial bus;

a second connector element connected to the serial bus; and a second signal acquisition unit connected to the second connector element and configured to receive a first precordial analog signal, a second precordial analog signal, a third precordial analog signal, a fourth precordial analog signal and a sixth precordial analog signal from a first, a second, a third, a fourth and a sixth precordial electrode, respectively, to receive said average voltage from said serial bus, to amplify said first precordial analog signal, said second precordial analog signal, said third precordial analog signal, said fourth precordial analog signal, and said sixth precordial analog signal to yield a first amplified precordial analog signal, a second amplified precordial analog signal, a third amplified precordial analog signal, a fourth amplified precordial analog signal and a sixth amplified precordial analog signal, respectively, to obtain a first compared amplified precordial analog signal as the potential difference between said first amplified precordial analog signal and said average voltage, to obtain a second compared amplified precordial analog signal as the potential difference between said second amplified precordial analog signal and said average voltage, to obtain a third compared amplified precordial analog signal as the potential difference between said third amplified precordial analog signal and said average voltage, to obtain a fourth compared amplified precordial analog signal as the potential difference between said fourth amplified precordial analog signal and said average voltage, to obtain a sixth compared amplified precordial analog signal as the potential difference between said sixth amplified precordial analog signal and said average voltage, to convert said first compared amplified precordial analog signal, said second compared amplified precordial analog signal, said third compared amplified precordial analog signal, said fourth compared amplified precordial analog signal, and said sixth compared amplified precordial analog signal to digital form to yield a second digital signal, and to provide said second digital signal via said second connector element to said serial bus.

2. The data acquisition system according to claim 1, wherein said serial bus is a Universal Serial Bus (USB).

3. The data acquisition system according to claim 2, comprising a patient monitor configured to receive data from the serial bus.

4. The data acquisition system according to claim 1, wherein a patient id is transferred to said first and second signal acquisition units for setting a patient context.

5. The data acquisition system according to claim 3, wherein the speed of said serial bus is low enough to allow connection from the first and the second signal acquisition units to the patient monitor without a hub electronic connection.

6. A method for obtaining electrophysiological signals from a patient, the method comprising:

receiving in a first signal acquisition unit a first analog signal, a second analog signal, a third analog signal, and a fourth analog signal from a first limb electrode, a second limb electrode, a third limb electrode, and a fourth limb electrode, respectively, and a fifth analog signal from a fifth precordial electrode;

amplifying in the first signal acquisition unit said first analog signal, said second analog signal and said third analog signal to yield a first amplified analog signal, a second amplified analog signal and a third amplified analog signal, respectively;

computing in the first signal acquisition unit an average voltage of said first amplified analog signal, said second amplified analog signal, and said third amplified analog signal;

amplifying in the first signal acquisition unit said fifth precordial analog signal to yield a fifth amplified precordial analog signal obtaining in the first signal acquisition unit a fifth compared amplified precordial analog signal as the potential difference between said fifth amplified precordial analog signal and said average voltage;

converting in the first signal acquisition unit said first amplified analog signal, said second amplified analog signal, said third amplified analog signal, and said fifth compared amplified precordial analog signal to digital form to yield a digital signal;

providing, from the first signal acquisition unit, said digital signal to a serial bus via a connector element;

providing, from the first signal acquisition unit, said average voltage to said serial bus via said connector element;

receiving in a second signal acquisition unit a first precordial analog signal, a second precordial analog signal, a third precordial analog signal, a fourth precordial analog signal, and a sixth precordial analog signal from a first precordial electrode, a second precordial electrode, a third precordial electrode, a fourth precordial electrode, and a sixth precordial electrode, respectively;

receiving said average voltage in said second signal acquisition unit from said serial bus;

amplifying in said second signal acquisition unit said first precordial analog signal, said second precordial analog signal, said third precordial analog signal, said fourth precordial analog signal and said sixth precordial analog signal to yield a first amplified precordial analog signal, a second amplified precordial analog signal, a third amplified precordial analog signal, a fourth amplified precordial analog signal and a sixth amplified precordial analog signal;

obtaining, in said second signal acquisition unit, a first compared amplified precordial analog signal as the potential difference between said first amplified precordial analog signal and said average voltage;

obtaining, in said second signal acquisition unit, a second compared amplified precordial analog signal as the potential difference between said second amplified precordial analog signal and said average voltage;

obtaining, in said second signal acquisition unit, a third compared amplified precordial analog signal as the potential difference between said third amplified precordial analog signal and said average voltage;

obtaining, in said second signal acquisition unit, a fourth compared amplified precordial analog signal as the potential difference between said fourth amplified precordial analog signal and said average voltage;

obtaining, in said second signal acquisition unit, a sixth compared amplified precordial analog signal as the potential difference between said sixth amplified precordial analog signal and said average voltage;

converting in said second signal acquisition unit said first compared amplified precordial analog signal, said second compared amplified precordial analog signal, said third compared amplified precordial analog signal, said fourth compared amplified precordial analog signal, and a sixth compared amplified precordial analog signal to digital form to yield a second digital signal; and providing said second digital signal via a second connector element to said serial bus from said second signal acquisition unit.

7. The method according to claim 6, the method further comprising:

expanding said first signal acquisition unit by a 12 lead ECG extension unit to form a full 12 lead ECG signal unit.

8. The method according to claim 6, wherein said serial bus is a Universal Serial Bus (USB).

9. The method according to claim 6, wherein the method further comprises the step:

augmenting said serial bus by an analog Wilson terminal.

10. The method according to claim 6, the method further comprising: setting up a wireless connection between a patient monitor and said serial bus.

11. The method according to claim 6, the method further comprising:

transferring a patient identification to said first signal acquisition unit during a wired connection thus setting the patient context.

12. The method according to claim 2, the method comprising:

arranging the speed of said serial bus to be low enough to allow a connection from the first signal acquisition unit or the second signal acquisition unit to the patient monitor without a hub electronic connection.

* * * * *